United States Patent [19]

Crossley

[11] Patent Number: 4,715,367
[45] Date of Patent: Dec. 29, 1987

[54] MULTIFUNCTIONAL BEHAVIORAL MODIFICATION DEVICE FOR SNORING, BRUXISM, AND APNEA

[76] Inventor: Robert B. Crossley, 6600 Elm Creek No. 152, Austin, Tex. 78744

[21] Appl. No.: 907,462

[22] Filed: Sep. 15, 1986

[51] Int. Cl.⁴ .............................. A61B 5/10; A61B 5/12
[52] U.S. Cl. ...................................... 128/136; 128/724; 128/419 R; 128/774; 128/733
[58] Field of Search .................. 128/132 R, 136, 137, 128/733 R, 774, 777, 782, 724, 419 R; 340/573, 575, 626, 665, 668

[56] References Cited

U.S. PATENT DOCUMENTS

| | | | |
|---|---|---|---|
| 3,480,010 | 11/1969 | Crossley | 128/136 X |
| 3,802,417 | 4/1974 | Lang | 128/724 X |
| 3,834,379 | 9/1974 | Granit | 128/132 R |
| 3,998,209 | 12/1976 | Macvaugh | 128/419 R X |
| 4,295,133 | 10/1981 | Vance | 340/575 X |
| 4,344,441 | 8/1982 | Radke | 128/733 |
| 4,381,788 | 5/1983 | Douglas | 128/782 X |
| 4,403,215 | 9/1983 | Hofmann et al. | 340/573 |
| 4,420,001 | 12/1983 | Hearne | 128/419 R X |
| 4,440,160 | 4/1984 | Fischell et al. | 128/132 R |
| 4,492,233 | 1/1985 | Petrofsky et al. | 128/774 X |
| 4,593,686 | 6/1986 | Lloyd et al. | 128/136 |

Primary Examiner—Robert A. Hafer
Assistant Examiner—Kathleen J. D'Arrigo

[57] ABSTRACT

A multifunctional behavioral modification device to diagnose, treat and monitor treatment for snoring, bruxism, or sleep apnea. Treatment consists of regulatable aversive shock, automatically occurring with each audible sound from snoring until snoring ceases or continuously but pulsatingly administered from clenching or grinding of teeth until the action ceases or continuously but pulsatingly administered from sleep apnea until breathing restarts. The placement of electrodes for administering the regulatable aversive shock is such so as to actuate a motor nerve thereby allowing use of a shock so mild as not to awaken a sleeper but sufficient to condition against the adverse behavior being sensed.

21 Claims, 6 Drawing Figures

MULTIFUNCTIONAL BEHAVIORAL MODIFICATION DEVICE FOR SNORING, BRUXISM, AND APNEA

BACKGROUND OF THE INVENTION

This invention comprises a basic device used with different sensing means to detect and treat snoring, bruxism or sleep apnea.

Bruxism has been defined as the non-purposeful grinding or clenching of teeth. This results in excessive teeth wear and in some cases loosening and loss of teeth. Other physical problems such as headaches and deterioration of jawbone joint also may occur. Of course the excessive grinding noise may also be deleterious to relationships with others as well.

Sleep apnea is a cessation of breathing during sleep that results in the person awakening for no reason he or she may be conscious of or of partial awakening or sleeping fitfully. Sleep apnea has been difficult to diagnose in a simple fashion. One of the objects of this invention is to allow simple diagnosis of sleep apnea.

The use of a mild electric shock or aversive stimulation to modify behavior is known in the arts. Snoring is, of course, easily detected by others. My U.S. Pat. No. 3,480,010 for a Snore Depressor is for a device to being about behavior modification or conditioning by administering an adjustable electrical shock with each snore sound with the shock being insufficient to awaken the sleeper. The subconcious mind associates the "punishment" of slight electrical shock with a snore sound and after a few night's use, the user becomes conditioned (behavior modification) to stop snoring. Usually this conditioning or behavior modification lasts several months before a short time re-use of the conditioning device becomes necessary.

Sleep apnea refers to non-breathing which occurs during sleep. It is a serious and sometimes life threatening disorder. Studies of thirty-five individuals suffering from sleep apnea in Stanford University's Sleep Disorder Clinic indicated the average number of episodes of non-breathing or sleep apnea ranged between 68 and 682 in a seven hour sleep period. The length of time of each episode lasted between 10 and 190 seconds.

With only a few exceptions, a medical examination will reveal no characteristic physical abnormalities in a person having sleep apnea. Therefore, at present the only means of detecting the condition is by clinical examination of observing the person while asleep. One object of the present invention is to provide a simple method for diagnosing sleep apnea that may be used by the patient himself.

There are two major types of sleep apnea. One, called "central sleep apnea" is relatively rare; the other, a more common and serious type is called "upper airway sleep apnea". Some success in treating "central sleep apnea" has been had with drugs. Treatment for "upper airway sleep apnea" involves a tracheotomy in which a hollow T tube is inserted in the trachea through a hole in the neck. The protruding end of the T tube is closed with a valve that may be opened at night so the person may then breath freely with air bypassing blockage of the upper airway.

Surgery is also used to treat "upper airway sleep apnea". In some cases enlarged folds of tissue at the top of the throat produce an obstruction during sleep. In these cases, surgery may be performed to cut away the excess folds of tissue. One physician has described this as a face lift on the throat. Both methods of treatment have obvious disadvantages. It is an object of this invention to use conditioning of the sub conscious mind to condition against or effectively treat both types of apnea.

Since apnea is usually accompanied by snoring, the invention makes it possible to treat both snoring and apnea in the same sleep period or to switch the snore sensor out of the circuit to diagnose or to treat sleep apnea alone.

In my U.S. Pat. No. 3,480,010, issued 11/25/1969 for an Electric Snore Depressor, an adjustable electric shock or aversive stimulation was used to condition a sleeper against snoring. Similarly, U.S. Pat. No. 3,834,379 issued 9/10/1974 to Mooza Grant describes aversive stimulation to inhibit self injurious behavior. In U.S. Pat. No. 4,440,160 issued to Fischell et al Apr. 3, 1984 aversive stimulation to condition against self injurious blows by the patient is described.

The present invention utilizes a regulatable electric shock for behavior modification reducing or eliminating snoring, bruxism, or sleep apnea and includes means to detect sleep apnea, bruxism, or snoring and monitor progress of the deconditioning behavioral modification. Further, placement of electrodes for administering a regulatable electric shock in the neckband or collar in this invention is such that the electrical stimulation of a motor nerve occurs allowing the use of a shock so mild that a sleeper is not awakened. Commercial use in my U.S. Pat. No. 3,480,010 for a Snore Depressor had shown that this effectively modified behavior to depress or completely eliminate snoring. We have added an electronic counter in order for a person to monitor his changes in behavior and modified the circuitry to allow similar type conditioning to alleviate bruxism and sleep apnea. The basic circuitry is enclosed in a collar with electrodes for administering a regulatable shock and separate means of sensing apnea and bruxism have been developed. The means for sensing snoring is built into the collar. Thus the Snore Depressor is improved by adding a counter to indicate progress in conditioning and the electronic circuitry is modified to allow use of conditioning by an electrical shock that is minimal enough not to waken the sleeper but will actuate a motor nerve to bring about conditioning to avert bruxism, or sleep apnea, or snoring. The methods of sensing bruxism and sleep apnea as well as use of an aversive stimulation to contact a motor nerve for conditioning against these is unique.

SUMMARY OF THE INVENTION

Prior art has been directed to treatment or conditioning to avert snoring or self inflicted injurious blows. This invention is directed toward non-clinical treatment of bruxism, apnea, or snoring. Among the objects of this invention are:

1. To provide simple means to diagnose sleep apnea without the necessity of clinical observation.
2. To provide non-clinical means to treat snoring, bruxism, or sleep apnea.
3. To provide simple means to monitor effectiveness of treatment of sleep apnea, bruxism, or snoring.
4. To provide means comfortable to wear to detect and treat snoring, bruxism, or sleep apnea.
5. To simplify manufacture of a device that may be used for diagnosis and treatment of snoring, bruxism, or sleep apnea.

6. To provide simple, safe, low-cost, means to diagnose and treat snoring or bruxism or sleep apnea without disturbing others in the room.

7. To use contact with a motor nerve to allow conditioning using an electrical shock that is mild enough not to awaken the user.

8. To provide a self contained, battery powered, treatment device to eliminate electrical hazards.

To accomplish these objectives the invention includes:

1. Battery powered circuitry contained in a flexible collar for automatically administering a regulatable electrical shock with a counter in the circuitry to monitor the number of times in a given period the shock is administered.

2. A bruxism sensor comprising dual pressure switches designed to be held in place on either side of the forehead and actuated by flexing of the temporal muscles as occurs in clenching or grinding of teeth.

3. A thin, flexible, lead, wire from the bruxism sensor to plug into the circuitry contained in the flexible collar.

4. A miniature microphone to sense breathing that connects with circuitry contained in the flexible collar to administer a pulsating electrical shock when breathing stops for a measured time and with shock continuing until breathing re-starts.

5. A user available adjustable unit to regulate the severity of the electric shock.

6. Electrodes so placed as to activate a motor nerve thereby allowing use of a low intensity shock that does not awaken the user, but will still bring about the desired behavior modification.

7. A microphone built in the neckband to detect a snore sound and switches and plug-in ports to allow use of the bruxism sensor and the breathing sensor. Note that usually the snore sensor, or microphone, which may be bypassed for apnea detection, is used along with the breathing sensor to treat apnea and snoring simultaneously.

This invention then comprises: a first unit in the form of a flexible collar containing battery powered circuitry and electrodes for administering a regulatable electrical shock that may be:

1. With each occurrence of the event, such as a snore sound which is picked up by the microphone in the flexible collar.

2. Pulsating, but continuous until a signal ceases, such as occurs with the bruxism detector, or sensor, which senses the temporal distention with clenching or grinding of teeth and continues until the muscles relax.

3. Pulsating, but continuous when a signal is NOT received, such as happens with the breathing sensor when breathing ceases for a period of time. The breathing sensor is a microphone that effectively senses airflow as well as sound.

As will be further described by the drawings and the claims the invention substantially meets the objectives are outlined. Modification of the circuitry to increase the shock with time if breathing does not re-start when using the device in the sleep apnea treatment mode would be within the spirit of this invention.

DETAILED DESCRIPTION OF THE DRAWINGS

Figure 1:
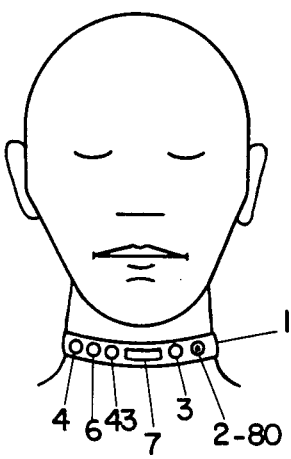
FIG. 1 shows a person wearing the basic collar unit of multifunctional behavioral modification device. The snore sensor microphone is built in this basic collar unit.

In FIG. 1 the basic collar unit 1 is illustrated fastened in place. The on-off switch 80 and electrode output adjustment 2 is shown located at the side of the unit. Location is not critical but is chosen for easy access for adjustment by the user. The bruxism sensor unit plug-in port 3 is adjacent to the on-off switch 80 and the electrode output adjustment 2. Physically, the on-off switch 80 and electrode output adjustment 2 are one unit. The breathing sensor unit plug-in port 4 and snore detector microphone bypass switch 6 are on the opposite end of the basic collar unit along with the snore detector microphone sensitivity adjustment 43. Location of these is not critical but they are also designed for easy user access. The plug-in ports are so designed that plugging in either the breathing sensor, which with associated circuitry becomes the apnea detector, or the bruxism detector inactivates the other one. Circuit details for this are not shown but would be obvious to one skilled in electronic arts. The Electronic counter 7 may be located as shown in the in use position.

Figure 2:
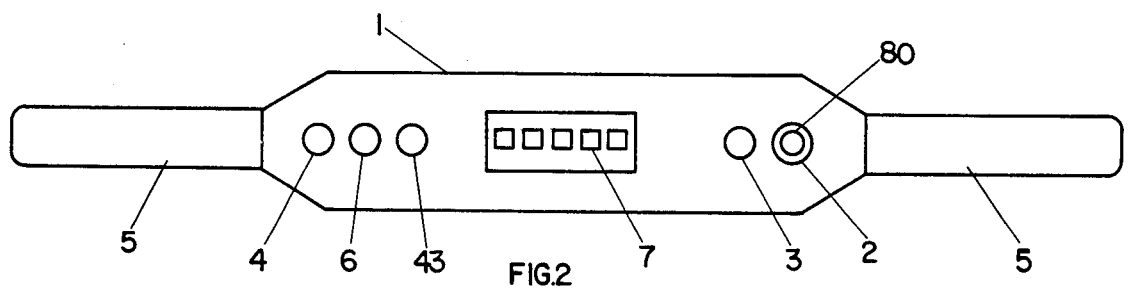
FIG. 2 shows a top view of the basic collar unit.

In FIG. 2 we've shown a top view of the basic collar unit showing approximate location of the on-off switch 80 and electrode output adjustment 2, the bruxism 30 detector plug-in port 3, the apnea sensor plug-in port 4, the snore detector microphone bypass switch 6, the snore detector microphone sensitivity adjustment 43, and an electronic counter 7. Straps 5 used for fastening the collar snugly around the user's neck are shown. In 35 a preferred embodiment Velcro straps are used, but many other type fasteners would be suitable.

Figure 3:
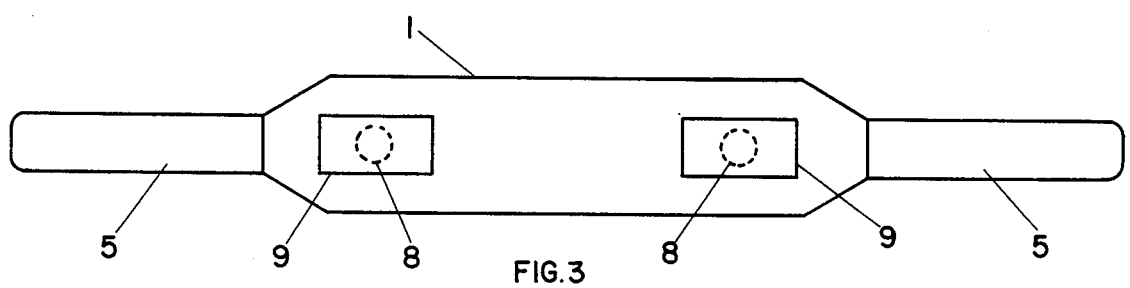
FIG. 3 shows a bottom view of the basic collar unit.

In FIG. 3 we've shown a bottom or inner view of the basic collar unit 1. The adjustable electric shock electrodes 8 are conveniently made using a rivet through the main body of the collar and connecting to the electronic circuitry. These electrodes 8 are covered with conductive plastic 9 in one embodiment but many other designs could be equally effective and are within the spirit of the invention. The location is such as to stimulate a motor nerve in the neck in normal usage. The snore sensor microphone is not shown, but is contained within the collar which shields the microphone from extraneous noise.

Figure 6:
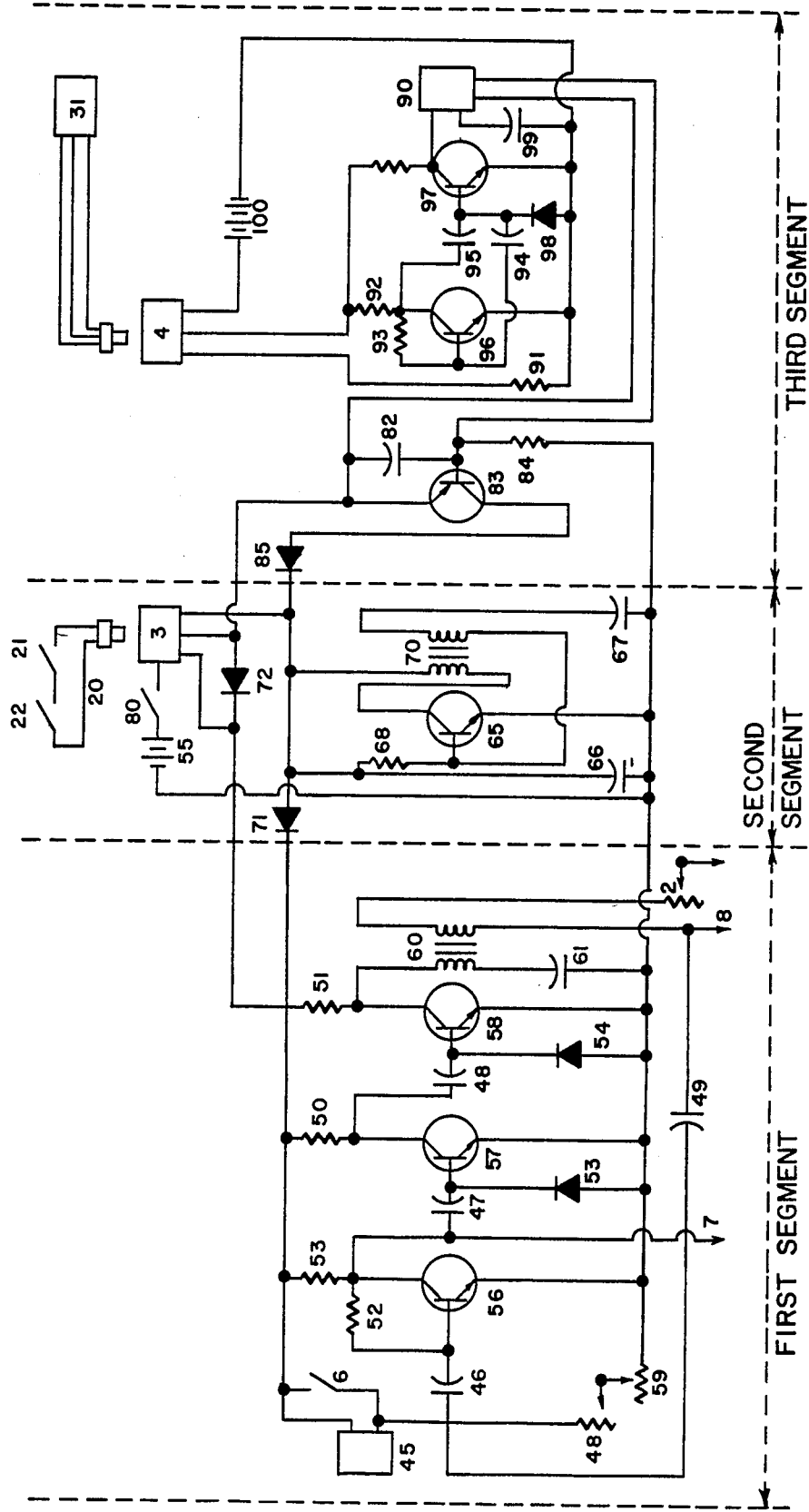
FIG. 6 shows the circuitry of the unit divided into segments to aid in explanations.

The basic collar unit may be conveniently made by slitting a sleeve like a piece of plastic as needed to insert the described components and the circuitry as shown in FIG. 6. The slits should be made on what becomes the underside of the collar unit 1. The slits may then be conveniently covered with a reusable adhesive-backed cloth. The cloth may then be temporarily removed for changing batteries. The fasteners 5 may be glued in the ends of the sleeve. Obviously, other techniques could be used and we do not mean to be limited to this style or method of manufacture.

Figures 4, 5:
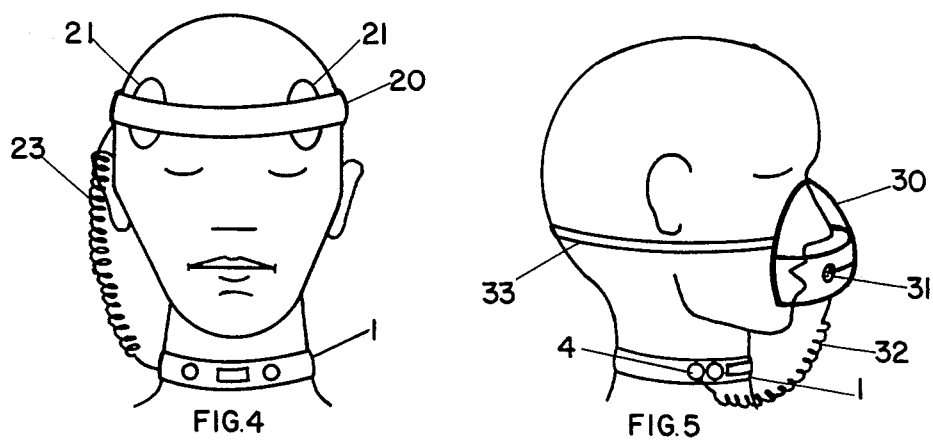
FIG. 4 illustrates a person wearing the dual pressure switch bruxism detector with the basic collar unit.
FIG. 5 illustrates a person wearing the breathing sensor unit with the basic collar unit.

In FIG. 4 we have shown the bruxism detector as it would be worn in use. The bruxism detector 20 is a pair of normally open pressure sensitive switches 21 and 22 that are moveably mounted on a band that can be conveniently worn around the forehead. The switches 21 and 22 are of a type where the user may adjust the sensitivity and are wired in series. A thin, flexible, electrically conductive wire 23 plugs into the basic collar unit. With clenching and grinding of teeth, the temporal muscles are flexed and switches 21 and 22 are activated to close from this temporal muscle action. It is necessary to have two switches in series to detect and/or treat bruxism since one switch could be closed by posistion of the wearer's head during sleep. When the switches 21 and 22 are closed with the plug in wire 23 plugged in port 3 of the basic collar unit 1, a pulsating regulatable electrical shock is administered until the temporal muscles relax thereby opening at least one switch. This results in conditioning the patient against bruxism. The Electronic Counter 7 indicates the number of times during a period, such as overnight, that the aversive shock is administered. Thus, a patient may see the improvement as it occurs over time.

In FIG. 5 we have shown the breathing sensor unit 33 in use and plugged into the basic collar unit 1. The sensor unit consists of microphone 31 and an open plastic coated metallic frame 30 designed to be worn comfortably with an elastic strap around the head. The purpose of the frame 30 is to hold the microphone 31 adjacent to, but not touching the nose or mouth. The microphone is designed to sense air flow from the mouth or nostrils. Plugging the lead wire 32 into the basic collar unit port 4 allows the unit to administer a continuous, but pulsating regulatable electric shock when breathing stops for a preset time and continues until breathing is resumed. Thus, the aversive pulsating shock conditions against sleep apnea.

The Electronic Counter 7 counts the number of times in a given period the adjustable electric shock is administered. Thus, with the breathing sensor unit in use, the basic collar 1 and Electronic Counter 7 detect sleep apnea. When used over a several day period the number of times activated each night can be used to monitor progress in the treatment. As will be seen from the circuitry as shown in FIG. 6 the snore sensor microphone bypass switch 6 is closed to detect and treat apnea alone. In normal usage, apnea and snoring are treated simultaneously. Note that with the switch 6 closed, the registration on the counter will occur only from apnea, thus we have both a diagnostic and treatment tool.

We have shown the circuitry as used in one embodiment of the invention in FIG. 6. It would be obvious to those skilled in electronics art to perform functions of the circuits shown in other ways such as using specially designed microprocessor chips or standard microprocessor chips in a hybrid circuit. By our description of a preferred embodiment we do not mean to be limited to details of the circuitry, but only to the purpose as outlined in the specifications and claims.

For ease of understanding and explanation we have shown in dotted lines the circuit separated into three segments.

In the first segment, we show the Snore Detector Microphone 45, and the external switch 6, which is opened to put the microphone 45 into the circuitry. Switch 6 is closed only to diagnose apnea and is normally open to treat snoring and apnea simultaneously. Variable resistors 59 which may be 500K and 43 which may be 100K are used to adjust the microphone 45 sensitivity. The variable resistor 59 is pre-set in the factory and the variable resistor 43 may be manually adjusted by the user.

The first segment also contains a known type transistorized amplification circuit utilizing three transistors 56, 57 and 58, two diodes 53 and 54, four 0.02 microfared capacitors 46, 47, 48 and 49, two 15K ohm resistors 50 and 51, one 44M ohm resistor 52, one 470K ohm resistor 53, one 22M microfared capacitor 61 and power supply, which may be 15 V from battery 55 in the second segment of the circuitry.

When the snore sound is picked up by the microphone 45 the electrical output from the microphone 45 is amplified resulting in relatively high potential in the secondary of the step up transformer 60. In turn a mild shock is administered through the electrodes 8. Note that the user may simulate snoring and with variable resistor 43 adjust the microphone sensitivity and with the variable resistor 2 adjust the severity of the shock. Note that physically variable resistor 2 and power switch 80 in the second segment are a normal switch and variable resistor in one unit. From the circuitry it may be seen that a louder snoring sound will result in greater output from the microphone and an increase in shock sent via the electrodes 8.

An Electronic Counter 7 is hooked into the circuit after the 1st amplification stage. In one embodiment a 555 CMOS Timer Chip was used with a CM0S 4553 3 digit counter, a CMOS 4543 BCD 7 segment decoder-driver and D0-D3 Amperix LC 513031 15/15 Liquid Crystal Display unit for the counter. A reset switch is provided. Details are not shown as electronic counters are well known to one of ordinary skill in electronics.

In the Second Segment, a pulsating current is generated as long as both bruxism detector switches 21 and 22, which plug into the bruxism sensing port 3, are closed. Pressure from tensing of the temporal muscles which occurs from teeth clenching and grinding, or bruxism, causes both pressure switches to close. The pressure switches 21 and 22 are in series since one could be closed by position of the users head. The pressure switches are of a type that allow the patient to adjust their sensitivity. As long as the switches are closed the pulsating current is generated. This pulsating current goes from the Second Segment to feed into the First Segment of the overall circuitry thereby causing the electrodes 8 to deliver a continuous but pulsating shock. This pulsating shock is administered through electrodes 8 until the temporal muscles relax allowing at least one of the buxism detector pressure switches 21 or 22 to open. Thus the person is conditioned against bruxism. Again the electronic counter 7 shows the number of times the circuit has been activated in a given period to allow the patient to monitor his rate of conditioning.

In one embodiment the pulse generating circuit in the Second Segment comprises a 22 microfared condenser 66, a D16P1 transistor 65, a 10 microfared condenser 67, a 470K ohm resistor 68, two diodes 71 and 72, a battery 55 which may be 15 volts and a step up transformer 70 hooked up as shown. When the bruxism detector 20 is plugged in dual switches 21 and 22 become part of the circuit. A multi-contact jack plug may be utilized for the plug in.

To use the device for conditioning against bruxism the user proceeds as follows:

1. Closes power switch 80 on the basic collar unit.
2. Straps the basic collar unit 1 firmly in place. (In a preferred mode, the electrodes 8 are moistened with a conducting gel before fastening the basic collar in place.)

3. Straps the bruxism detector unit 20 around his forehead and adjusts the location of the pressure switches 21 and 22 so that they receive maximum pressure from flexing the temporal muscles.

4. Plugs the lead wire 23 into plug-in port 3.

5. Adjusts sensitivity of the pressure switches 21 and 22 so that a slight pressure closes the switches to activate the basic collar unit 1. The amount of shock may be re-adjusted using variable resistor 2.

6. The counter 7 may be re-set to 0 to monitor activation.

With the procedures as outlined the unit then administers an aversive pulsating regulatable electrical shock in response to bruxism.

The Third Segment, used for apnea detection and treatment contains an amplifier circuit and a timer circuit of a transistor type. When the breathing detector or sensor 33 is plugged into port 4, the battery 100 which may be 12 V and the breathing sensor microphone 31 is put into the amplifier circuit of the Third Segment and at the same time power from battery 55 in the Second Segment feeds into the timer circuit in the Third Segment. For the sake of clarity wiring details for Port 3 and Port 4 are not shown but would be easily supplied by one of ordinary skill in the electronics art. Not shown but within the spirit of the invention would be an addition to the circuitry to automatically increase the severity of shock as the length of time before breathing re-starts increases.

In operation the airflow indicating breathing is picked up by the breathing detector microphone 31, and amplified in two stage amplification to operate a relay 90 which may be a 5 volt relay. The amplification circuit may be comprised of two D16P1 transistors 96 and 97, a diode 98, one 44M ohm resistor 93, one 220K ohm resistor 92 and one 100K ohm resistor 91, two 0.02 MF capacitors 94 and 95 and one 22 MF capacitor 99. A separate 12 V battery 100 may be used to power this circuit.

When air flow from breathing is picked up by the breathing detector microphone 31 and the signal is amplified to operate the relay 90 and the relay is set up to act as a switch which "resets" the time delay circuit.

The time delay circuit may be powered by the same 15 V battery 55 used to power the circuits in the First Segment. The time delay circuit may be comprised of one transistor 83, one diode 85, one 220 MF capacitor 82 and one 590K ohm resistor 84. The resistor 84 may be varied to change the delay time but with the 590K ohm resistor delay should be about 15 seconds. The circuits in the Third Segment then operate so that over about 15 seconds the 220 MF capacitor will charge and allow current to carry through the transistor 83 and diode 85 to activate the pulsating current generator of the Second Segment which in turn activates the basic unit to deliver a continuous pulsating shock through electrodes 8 while registering on the counter 7. If breathing occurs before the 15 second time delay occurs the amplification circuit operates the relay 90 to close two contact points so that the 220 MF capacitor 82 is allowed to bleed off to ground so that there is no current flow through transistor 83 and diode 85. Thus no shock is administered as long as breathing continues but if breathing stops for a period which may be about 15 seconds with the particular circuit components a continuous pulsating regulatable electrical shock is administered through electrodes 8 until breathing resumes. Thus the wearer is conditioned against sleep apnea with counter 7 allowing him to monitor the total number of shocks administered in the one or more times he stopped breathing for the length of time set by the timer circuit or about 15 seconds in one embodiment.

The circuit as outlined may be used to diagnose as well as treat apnea. Now quite generally snoring and sleep apnea are associated and by leaving the snore detector microphone in the circuit the user is in any one period conditioned against both snoring and sleep apnea. In this case the counter counts the times that shock is administered for both apnea and snoring.

For diagnosis the snore detector microphone bypass switch 6 is closed and the unit then administers a pulsating oversize shock only from temporary cessation of breathing or apnea. The record of shock pulses on counter 7 then indicates presence of apnea.

What is claimed is:

1. A multifunctional behavioral modification device comprising:
   A. a means for detecting clenching and grinding of teeth
   B. a means for detecting snoring
   C. a means for detecting breathing
   D. a pair of electrodes suitable for skin contact for administering an adjustable electric shock
   E. battery power means
   F. battery powered circuitry suitable for impressing an adjustable electric shock across said electrodes when activated by one of the following:
      1. said means for detecting clenching and grinding of teeth
      2. said means for detecting snoring
      3. said means for detecting breathing indicating that breathing has stopped
   G. an electronic counter means for counting the number of times in a given period a current is impressed across said pair of electrodes
   H. an enclosure means for said battery powered circuitry.

2. A multifunctional behavioral modification device as in claim 1 where said enclosure means comprises:
   A. a flexible electrically insulating enclosure suitable for containing said battery powered circuitry, said battery power means, said electronic counter, said pair of electrodes, a first plug-in port for said means for detecting clenching and grinding of teeth and for said means for detecting a snore sound, a second plug-in port for said means for detecting breathing, a switch to activate said battery powered circuitry, a bypass switch to bypass said means for detecting snoring, and means to externally adjust the severity of said adjustable shock
   B. means for removeably fastening said flexible electrically insulating enclosure around the next of a person
   C. a means for resetting sid electronic counter.

3. A multifunctional behavioral modification device as in claim 2 where said means to adjust said adjustable electric shock across said electrodes is a first externally adjustable resistor.

4. A multifunctional behavioral modification device as in claim 3 where each of said pair of electrodes comprise metal covered with a soft electrically conductive material placed in either end of said flexible insulating enclosure so that said pair of electrodes make skin contact when said flexible insulating enclosure is fastened snugly around the user's neck.

5. A multifunctional behavioral modification device as in claim 4, where said pair of electrodes are so placed as to activate a motor nerve in the neck.

6. A multifunctional behavioral modification device as in claim 5 where said battery powered circuitry comprises:
   A. saidmeans for detecting snoring
   B. said bypass switch from said means for detecting snoring to a first segment of said circuitry
   C. said first segment further comprising said battery power means, a second externally adjustable resistor to adjust the sensitivity of said means for detecting snoring, a first amplifier circuit leading to a step-up transformer with output leading through said first externally adjustable resistor to said pair of electrodes for administering said adjustable electric shock, and said electronic counter taking off from said amplifier circuit to count the number of times in a given period said adjustable electric shock is administered
   D. a second segment connected to said first segment powered by said battery power means and comprising said first plug in port for connecting said means for detecting clenching and grinding of teeth to a pulse generator circuit to generate a pulsating current and send said pulsating current to said amplifier circuit in said first segment to administer a pulsating electric shock through said pair of electrodes as long as said means for detecting clenching and grinding of teeth is activated
   E. a third segment of said circuitry, comprising: said battery power means, electronic circuitry to detect interruption of a signal from said means for detecting breathing, said second plug in ports for said means for detecting breathing connected to a second amplifier circuit to amplify a signal picked up from said means for detecting breathing to operate a relay, said relay operating to reset a time delay circuit, said time delay circuit if not reset operating to feed a signal to said pulse generator circuit of said second segment, in turn said pulse generator circuit operating to feed a pulsating signal to said first segment to administer a continuous pulsating shock through said pair of electrodes until said timer circuit is reset by said means for detecting breathing indicating that breathing has re-started.

7. A multifunctional behavioral modification device as in claim 6 where said electronic counter is a resettable Liquid Crystal Display Electronic Counter.

8. A multi functional behavioral modification device as in claim 6 where said means for detecting clenching and grinding of teeth comprises:
   A. a pair of normally open pressure switches wired in series, having adjustable sensitivities and mounted on a removeable adjustable headband designed to have said switches moveably mounted so as to have one switch contact each temple of the wearer's head with said switches being activated by flexing of the temporal muscles that occurs with clenching and grinding of teeth
   B. a flexible electrically conductive line leading from said pair of switches to removeably plug-in to said first plug in port of said flexible electrically insulating enclosure.

9. A multifunctional behavioral modification device as in claim 8 where said means for detecting snoring comprises:
   a microphone built into said battery powered circuitry and so positioned in said flexible electrically insulating enclosure to pick up audible sound from snoring while minimizing effect of extraneous sounds.

10. A multifunctional behavioral modification device as in claim 9 where said means for detecting breathing comprises:
    A. a miniature microphone with means for holding said miniature microphone adjacent to the wearer's mouth and nostrils
    B. a flexible electrically conductive line leading from said miniature microphone to removeably plug into said second plug-in port in said flexible electrically insulating enclosure of said multifunctional behavioral modification device.

11. A multifunctional behavioral modification device as in claim 10 where said battery powered circuitry is activated only when both of said pair of pressure switches are closed and where said circuitry delivers said pulsating, regulatable shock through said electrodes until said temporal muscles relax allowing at least one of said pair of switches to open.

12. A multifunctional behavioral modification device comprising:
    A. a primary circuit means suitable for receiving repetitive electronic signals from a first transducer and administering a regulatable aversive shock with each signal through a pair of electrodes
    B. a secondary circuit means to generate a pulsating signal from a continuous signal from a second transducer and to put said pulsating signal into said primary circuit means to administer a pulsating regulatable aversive shock through said pair of electrodes as long as said second transducer signal is received into said secondary circuit means
    C. a tertiary circuit means to generate a signal to feed into said secondary circuit means when a normally received signal from a third transducer is interrupted for a regulatable length of time
    D. means to connect said first transducer into said primary circuit means
    E. a first plug-in port to connect said second transducer with said secondary circuit means
    F. a second plug-in port to connect said third transducer to said third circuit means
    G. a primary switching means to allow use of said first transducer with said primary circuit means
    H. a secondary switching means to allow use of said second transducer with said secondary circuit means feeding into said primary circuit means
    I. a tertiary switching means to allow use of said third transducer with said third circuit means feeding into said secondary circuit means and then into said primary circuit means to administer a pulsating regulatable aversive shock when said normally received signal from said third transducer is interrupted for a regulatable length of time
    J. battery means to power said primary circuit means, said secondary circuit means and said tertiary circuit means.

13. A multifunctional behavioral modification device as in claim 12 where said primary circuit means, said tertiary circuit means, said first transducer, said first plug-in port, said second plug-in port, said battery means, and a said pair of electrodes suitable for skin contact are contained inside a flexible strap with means for fastening said strap to wearers body to provide body contact for said electrodes.

14. A multifunctional behavioral modification device as in claim 13, where said flexible strap is suitable for fastening around the user's neck.

15. A multifunctional behavioral modification device as in claim 14 where a resettable electronic counter means is connected with said primary circuit means to count the number of times in a given period said regulatable aversive shock is administered from said primary circuit means and to count the number of times said pulsating regulatable aversive shock is administered from said secondary circuit means feeding into said primary circuit means.

16. A multifunctional behavioral modification device as in claim 15 where the severity of said regulatable aversive shock and said pulsating regulatable aversive shock may be externally adjusted by the user.

17. A multifunctional behavioral modification device as in claim 16 where said pair of electrodes are so placed in said flexible strap so as to activate a motor nerve in the neck from said regulatable aversive shock.

18. A multifunctional behavioral modification device as in claim 17 where said first transducer is a microphone suitable for detecting a snore sound.

19. A multifunctional behavioral modification device as in claim 18 where said second transducer is a pair of pressure switches that may be operated by tensing of the temporal muscles with said pressure switches hooked in series so that current may flow only when both switches are closed.

20. A multifunctional behavioral modification device as in claim 19 where said pressure switches are of an adjustable sensitivity type.

21. A multifunctional behavioral modification device as in claim 19 where said third transducer is a microphone capable of detecting the air flow from breathing when placed adjacent to the user's mouth and nostrils.

* * * * *